United States Patent [19]

Sigl

[11] 4,412,881
[45] Nov. 1, 1983

[54] METHOD AND APPARATUS FOR MANUFACTURING ELASTIC LEG DISPOSABLE DIAPERS

[75] Inventor: Wayne C. Sigl, Winnebago County, Wis.

[73] Assignee: Kimberly-Clark Corporation, Neenah, Wis.

[21] Appl. No.: 278,619

[22] Filed: Jun. 29, 1981

[51] Int. Cl.³ .......................................... B32B 31/08
[52] U.S. Cl. .................................. 156/164; 156/229; 156/270; 156/291; 156/495; 156/497; 156/522; 156/554
[58] Field of Search ............... 156/164, 495, 229, 269, 156/270, 291, 522, 497, 554, 516; 83/13, 54, 701

[56] References Cited

U.S. PATENT DOCUMENTS 4,081,301  3/1978  Buell ................................ 156/164
4,227,952 10/1980  Sabee ............................... 156/164
4,240,866 12/1980  Rega ................................ 156/164
4,360,398 11/1982  Sabee ............................... 156/164

Primary Examiner—Jerome W. Massie
Attorney, Agent, or Firm—Richard C. Ruppin

[57] ABSTRACT

A method and apparatus for elasticizing the leg areas of disposable diapers is disclosed. A continuously moving elastic ribbon is attached to a continuously moving web at spaced apart locations along the length of the web corresponding to the leg areas of a finished diaper. The web is moved over an arcuate surface and the portion of the ribbon that is not attached to the web is drawn through a gap in the surface so that the unattached ribbon portion separates from the web and travels a shorter path than the web. While the web and unattached ribbon portion are separated, the unattached ribbon portion is cut so that only the ribbon portion attached to the web will have an elasticization effect on the finished diapers.

16 Claims, 10 Drawing Figures

METHOD AND APPARATUS FOR MANUFACTURING ELASTIC LEG DISPOSABLE DIAPERS

FIELD OF THE INVENTION

This invention relates to an apparatus and method for elasticizing only the leg areas of disposable diapers and in particular to an apparatus and method for removing elastic from other than the leg areas of a disposable diaper where it is not desired to have elastic. The subject matter of this application is related to that of application Ser. No. 278,753, by W. J. Moore, assigned to the same assignee as that of the instant invention.

BACKGROUND OF THE INVENTION

Due to the improved fit and fluid sealing properties provided by leg elasticization, manufacturers of disposable diapers have, in recent years, developed various methods and apparatus for attaching elastic strips to the leg areas of the diapers. Because of the the speed, continuous nature of diaper manufacturing methods, virtually all of the commercially practicable processes have utilized a continuous elastic ribbon affixed to the diaper in the leg areas and subsequently cut either prior to or as a part of the severing of the continuous web into separate diapers. Typical of these processes and apparatus is that disclosed in U.S. Pat. No. 4,081,301 to Buell. This patent discloses adhering of the continuous elastic ribbon only in discrete, intermittent areas corresponding to the leg areas in a finished diaper. The ribbon and the diaper are then simultaneously cut at the waist of the diaper when the continuous web is cut into separate diapers. The drawback of this process is that it is inefficient from the material use aspect in that it leaves an unneeded length of elastic attached to the diaper. Another approach to handling the problem is disclosed in U.S. Patent No. 4,227,952 to Sabee. In the method of this patent, the elastic ribbon is continuously applied to the web, however, before the attachment of the ribbon to the web, the latter is folded in the areas of the web corresponding to the waist areas of the finished diapers. Consequently, the elastic ribbon is attached to the web only in the leg areas of the finished diaper. The elastic ribbon is then severed at the points opposite the folded areas of the web and the web is then unfolded so that elastic is only in the leg areas and the waist areas contain no unneeded elastic. The problem with this method and the apparatus used in it is that it is quite complex and difficult to operate at high speeds required for commercial usefulness.

It is a principal object of this invention to provide a method and apparatus for attaching a continuously moving elastic ribbon to a continuously moving web only in the areas of the web corresponding to the leg areas in finished diapers and removing the portions of the elastic ribbon between the attached areas in a simple and commercially practicable manner.

SUMMARY OF THE INVENTION

The objective of the invention is accomplished by providing an apparatus in which the elastic ribbon and web are continuously moved together and the ribbon attached at spaced apart locations on the web corresponding to the leg areas of the finished diaper. While the web and the elastic ribbon are moving together, the web is separated from the ribbon in the areas of the ribbon that are not attached to the web. The separating of the web from the unattached portions of the ribbon is accomplished by supporting the web on a surface which causes the web to move along a path having a longer length than the length of the path of movement of the unattached portions of the ribbon. To permit the unattached portions of the ribbon to move this shorter distance, a gap is provided in the supporting surface through which the unattached ribbon portions pass so that separation occurs. While the unattached portions of the ribbon are thus separated from the web, both ends of unattached portions of the ribbon may be cut, preferably adjacent the location of the attached portions of the ribbon, and the unattached portions of the ribbon may then be removed.

BRIEF DESCRIPTION OF THE DRAWINGS

Further objects and advantages of the invention will appear when taken in conjunction with the accompanying drawings, in which.

DETAILED DESCRIPTION OF THE INVENTION

Figure 9:
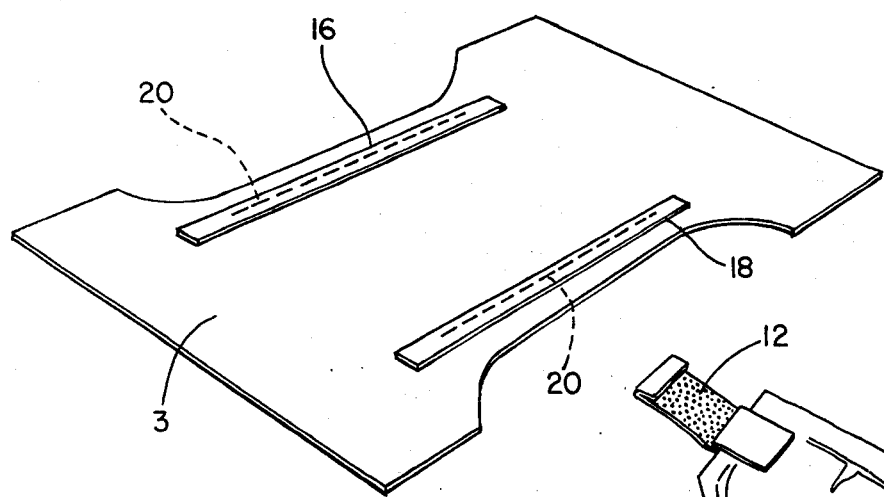
FIG. 9 is a perspective view showing the backsheet of a disposable diaper, which comprises a section of the web, with elastic strips attached in the leg areas.
Figure 10:
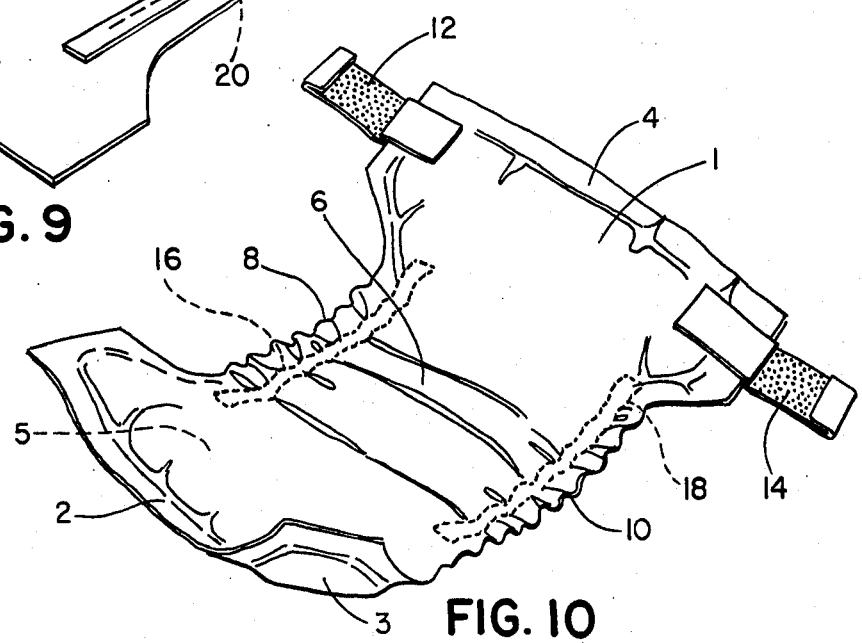
FIG. 10 is a perspective view of a finished elasticized leg disposable diaper just prior to its fitting onto a wearer.

For purposes of background, the elasticized leg diaposable diaper produced by the apparatus and method of the invention will first be discussed. Referring first to FIGS. 9 and 10, there is shown in FIG. 10 a disposable diaper having a topsheet 1, a backsheet 3, an adsorbent pad 5 between the topsheet 1 and backsheet 3, a front waist area 2, a rear waist area 4, and a crotch area 6 intermediate the two waist areas. Leg areas 8 and 10 are positioned laterally of the crotch area 6 and intermediate of the waist areas 2 and 4. Waist fastened tapes 12 and 14 are bonded to the corner areas 5 of the rear waist area 4 and are fastenable to the front waist area 2 when the diaper is fitted to a wearer to secure the diaper on the wearer. Elastic strips 16 and 18 are attached substantially parallel to the length of the diaper in the leg areas 8 and 10 respectively, as shown in FIG. 9, to elasticize the leg areas of the diaper and provide a snug fit around the legs of a wearer. In FIG. 10, the elastic strips 16 and 18 are shown in a relaxed condition in which they cause random pleating or folding of the topsheet 1 and backsheet 3.

In FIG. 9, the only diaper components shown are the backsheet 3, the elastic strips 16 and 18 and adhesive lines 20 and 20 respectively attaching the elastic strips 16 and 18 to the backsheet 3. The backsheet 3 and the elastic strips 16 and 18 are shown in an extended, flat condition in which the elastic strips 16 and 18 are stretched.

Referring now generally to FIGS. 1-5, apparatus is shown for supplying a web 28 and elastic ribbons 30 and 32, attaching the ribbons 30 and 32 to the web 28, the removing portions of the ribbons 30 and 32 which are not attached to the web 28. Apparatus for applying the absorbent pad 5, the waist fasteners 12 and 14, and the topsheet 2 are not shown or described herein inasmuch as they form no part of the present invention and may be of types that are well known in the art. Also, the apparatus and method will be described with reference to FIGS. 1-5 only, in most instances, with respect to continuous elastic ribbon 32 since the method and the operation of the apparatus is the same for both of the ribbons 30 and 32.

Figure 1:
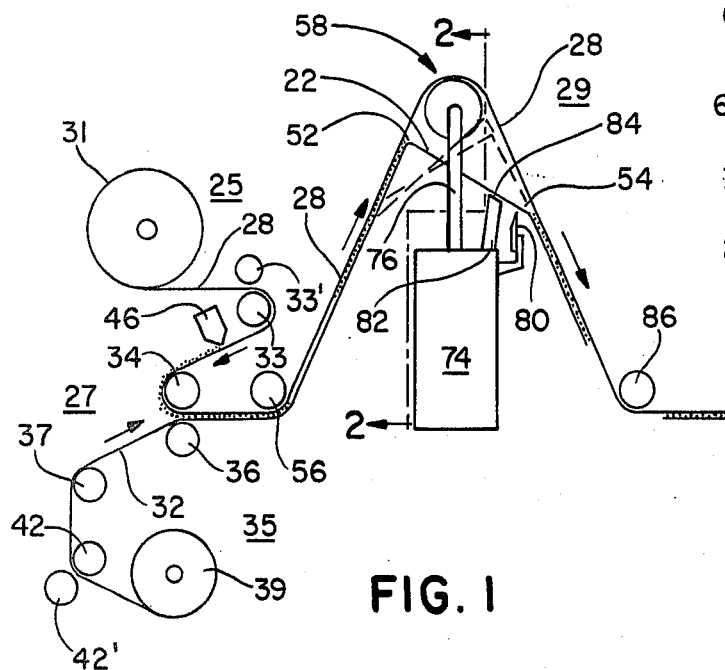
FIG. 1 is a simplified side elevation view showing the web supply, elastic supply, elastic bonding, and elastic removal stations of the diaper manufacturing apparatus of the invention.
Figure 2:
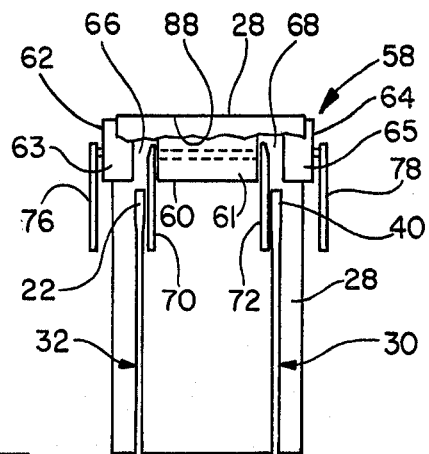
FIG. 2 is a cross-sectional view taken along section line 2—2 of FIG. 1 and showing only the elastic removal station.

In FIG. 1 is shown a web supply station 25 at which the web material 28 is drawn from a supply roll 31 by feed rolls 33 and 33' and fed to the elastic attaching station 27. At the elastic ribbon supply station 35, the elastic ribbon 32 is drawn from supply roll 39 by feed rolls 42 and 42'. The elastic ribbon 32 is then passed over a tension sensing roll 37 which, through feedback means (not shown), controls the speed of the feed rolls 42 and 42' such that the elastic ribbon 32 is maintained under tension as it moves with the web 28 through the elastic attaching station 27 and the elastic removal station 29.

Figure 8:
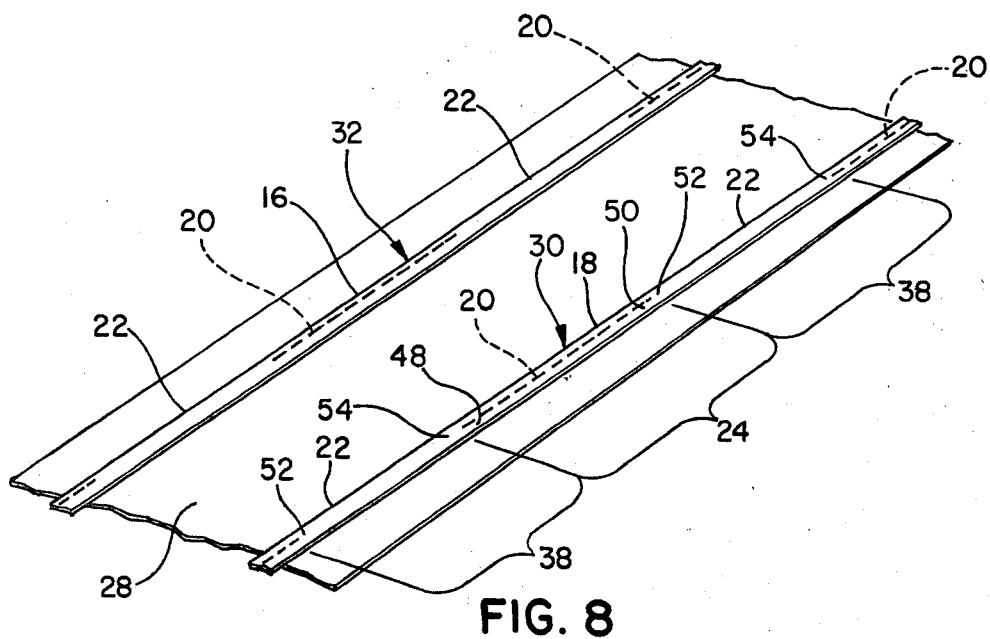
FIG. 8 is a perspective view of the web and elastic ribbons illustrating the attached and unattached portions of the ribbon.

At the elastic attaching station 27, adhesive nozzles 46 apply adhesive lines 20 to the web 28 along paths substantially parallel to the length of the web 28 and its direction of travel (see FIG. 9). The nozzles 46 operate such that adhesive is applied to the web 28 only at spaced apart locations 24 along the length of the web 28, as illustrated in FIG. 8. The spaced apart locations 24 on the web 28 correspond to the leg areas 8 and 10 of the finished diapers. Subsequent to the application of the adhesive lines 20 to the web 28, the web 28 and the elastic ribbon 32 are moved together through a pair of nip rolls 34 and 36 which press the web 28 and the elastic ribbon 32 together to thereby attach or bond the ribbon 32 to the web 28 only along the spaced apart locations 24 to which the adhesive lines 20 have been applied. Thus, there are portions 22 of the elastic ribbon 32 along locations 38 of web 28 which are unattached to the web 28 between the attached portions or strips 16 and 18 (see FIG. 9) along locations 24 on the web 28. As is best illustrated in FIG. 8, the attached elastic portions 16 and 18 of ribbons 30 and 32 on the web 28 have ends 48 and 50 and the unattached portions 22 of ribbon 30 have ends 52 and 54.

After attaching of the elastic ribbon 32 to the web 28, it is passed around idler roll 56 and to elastic removal station 29. The elastic removal station 29 includes a split roll 58 having a center roll 60, outboard rolls 62 and 64, and a gap 66 between outboard roll 62 and center roll 60 and gap 68 between outboard roll 64 and center roll 60. The rolls 60, 62, and 64 respectively have cylindrical surfaces 61, 63 and 65. The center roll 60 is rotatably supported on arms 70 and 72 which are in turn supported on a frame section 74 of the diaper production apparatus. Outboard rolls 62 and 64 are respectively rotatably supported on arms 76 and 78. A cutting means 80 for severing the unattached elastic portions 22 is also mounted on the frame section 74 and preferably is of a hot wire cutting type. In addition, a vacuum means 82 is mounted on the frame section 74 and includes a suction opening 84 positioned adjacent to the path of movement of the unattached elastic portions 22 of ribbon 30 for holding the elastic portions 22 and removing them subsequent to their cutting by the cutting means 80, as will be described in greater detail with reference to FIGS. 3-5. Upon removal of the unattached elastic portions 22, the web 28 will have attached to it only elastic portions or strips 18 and 16. The web 28 and elastic strips 18 and 16 then exit the elastic removal station 29 and pass around idler roll 86 to move toward additional stations of the diaper manufacturing apparatus. At the additional stations, other components will be added and further operations will be performed to produce a finished elasticized leg diaper.

Figure 3:
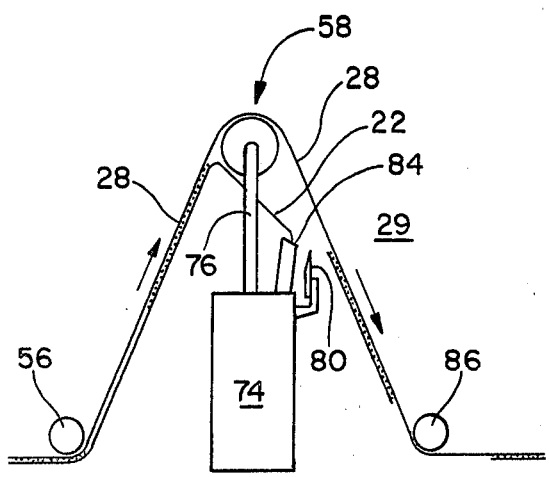
FIG. 3 is a simplified side elevation view similar to FIG. 1 showing only the elastic removal station just subsequent to the cutting of the elastic ribbon at its leading end.
Figure 4:
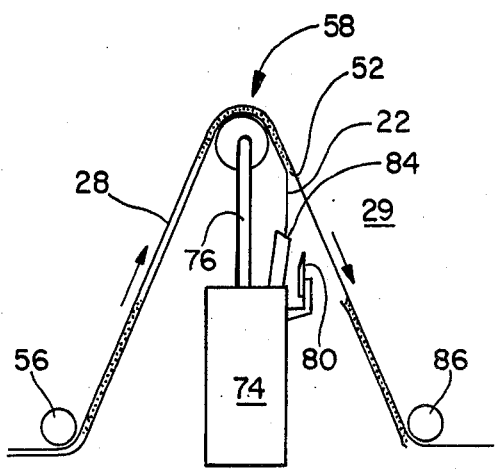
FIG. 4 is a simplified side elevation view similar to FIG. 3 showing the elastic removal station just prior to the cutting of the trailing end of the unattached portion of the elastic ribbon.
Figure 5:
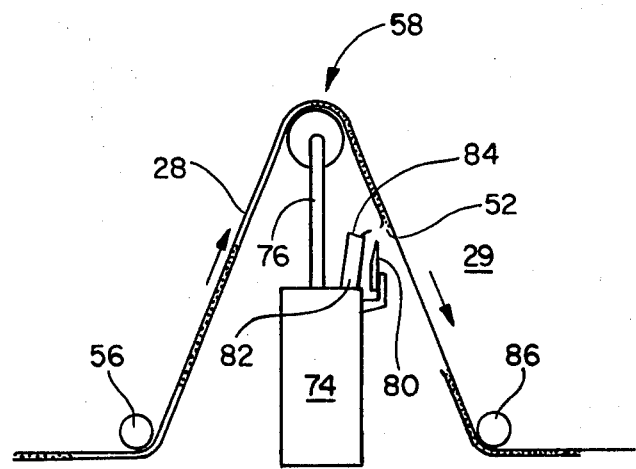
FIG. 5 is a simplified side elevation view similar to FIGS. 3 and 4 showing the elastic removal station as the trailing edge of the unattached portion of the elastic ribbon is being cut and just prior to removal of the unattached portion of the ribbon from the web.

Considering FIG. 1 further and also with reference to FIGS. 3-5, as the web 28 moves over the split roll 58, the portion of the elastic ribbon 32 that is attached to the web 28 will also move with the web over the split roll 58. However, the unattached portions 22 of the elastic ribbon 32 are free to separate from the web 28 and move through the gap 66. As may be seen by the phantom lines in FIG. 1, as the portion of the web 28 opposite the leading end 54 of one elastic portion 22 starts over the cylindrical surfaces 61, 63 and 65 of the split roll 58, the elastic portion 22 begins to separate from the web 28. As the web 28 progresses along its path further around the split roll 58, the separation of the unattached elastic portion 22 increases. The web 28 thus is supported by the surfaces 61, 63 and 65 of the split roll 58 to move along a path which is longer than the path of movement of elastic portions 22. It may be noted that the unattached elastic portions 22 will tend to move through the gap 66 merely by virtue of gravity. However, where the elastic ribbon 32 and therefore the unattached elastic ribbon portions 22 are stretched, the opportunity for the elastic portions 22 to follow a shorter path and thereby relax from the stretched condition will provide a more positive inducement for them to move through the gap 66 and follow the shorter path. As the unattached elastic portions 22 move along their shorter path, their leading ends 54 will contact the cutting means 80 and be severed from the continuous ribbon 32. At approximately the time of cutting of the leading end 54 of the elastic portion 22, the elastic portion 22 will be held by the vacuum means 82 due to the suction at suction opening 84 and removal of the elastic portion 22 will be initiated as shown in FIG. 3. As the web 28 continues over the surfaces of the split roll 58, the trailing end 52 of the elastic portion 22 will also move toward and into contact with the cutting means 80 and will be severed from the web 28 and ribbon 32, as shown in FIGS. 4 and 5. While the web 28 is continuing its movement over the split roll 58, the vacuum means 80 continues to carry away the elastic portion 22. Removal of the unattached elastic piece 22 is completed by the vacuum means 80 upon severing of the trailing end 52.

Figure 6:
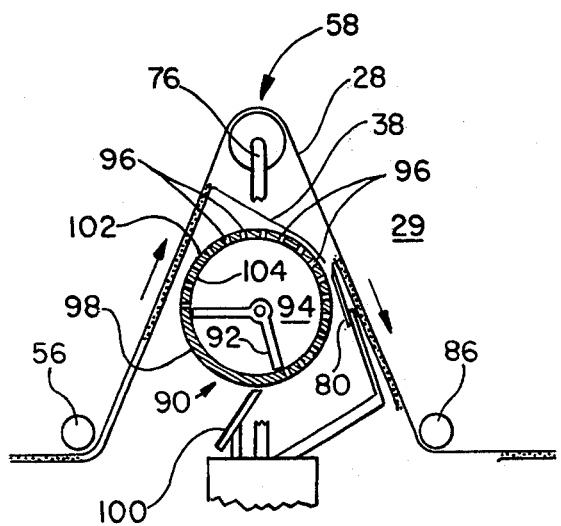
FIG. 6 is a simplified side elevation view of another embodiment of the invention showing only the elastic removal station while the elastic ribbon is being held by a vacuum drum and just subsequent to the cutting of the leading end of the unattached portion of elastic ribbon.
Figure 7:
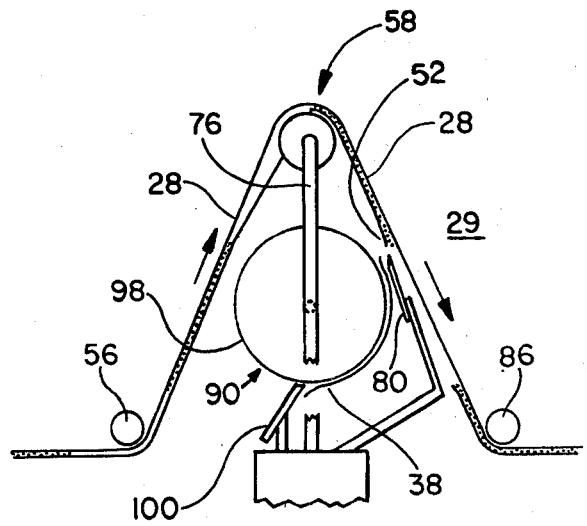
FIG. 7 is a simplified elevation view similar to FIG. 6 showing the position of the unattached portion of elastic ribbon just subsequent to the cutting of the trailing end of elastic ribbon and the removal of the cut ribbon piece by the vacuum drum.

In FIGS. 6 and 7 is shown another embodiment of the invention in which a rotating vacuum drum 90 is positioned at the elastic removal station 29 to hold and remove the unattached elastic portions 22 as they move toward and are severed by the cutting means 80. The rotating vacuum drum 90 includes a stationary internal section 92 forming a vacuum compartment 94 and a rotating cylindrical wall 98 having an exterior surface 102, an interior surface 104 and a plurality of openings 96 extending through the wall 98. The vacuum compartment 94 has a length in a circumferential direction such that, as the cylindrical wall 98 rotates and the openings 96 move over the vacuum compartment 94, the elastic ribbon portion 22 will be held and moved out of the short path it would normally follow to thereby apply tension to the elastic portion 22 as it approaches and is cut by the cutting means 80. This increase of tension on the elastic portion 22 will increase the speed of the cut. The vacuum compartment 94 extends a sufficient distance adjacent to the circumference of the drum 90 such that the elastic portion 22, after its leading end 54 is cut, will be held and drawn away from the web 28 so that tension is also applied to the elastic portion 22 as the cutting of the trailing end 52 occurs. After the final cut at end 52, its removal is completed by continued rotation of the cylindrical wall 98 past a scraper 100 which detaches the ribbon piece 22 from the drum.

An apparatus and a method is thus provided for elasticizing only the leg areas of a disposable diaper in which the elastic ribbon that is not needed in the waist area of the diaper is entirely removed. The apparatus and method are quite simple so that they can be readily and economically incorporated into a high speed diaper production apparatus.

It will be understood that the foregoing description of the present invention is for purposes of illustration only and that the invention is susceptible of a number of modifications or changes, none of which entail any departure from the spirit and scope of the present invention as defined in the hereto appended claims.

What is claimed is:

1. In an apparatus for manufacturing elastic leg disposable diapers including means for continuously moving a web of material in the direction of its length and means for attaching portions of a continuously moving elastic ribbon to the web at predetermined spaced apart locations along the length of the web, said predetermined locations corresponding to the leg areas of the finished diapers, the combination comprising:
   means acting in the web for separating the path of movement of the web and the elastic ribbon between said attached locations; and
   means for removing the unattached portions of the elastic ribbon between said attached locations while the unattached portions are separated from the web whereby the elastic ribbon will have an elasticization affect on the web only along said attached locations corresponding to the leg areas of the finished diapers.

2. The combination according to claim 1 wherein said separating means comprises means for supporting only the web.

3. The combination according to claim 1 wherein said separating means comprises means supporting the web along a first path, said supporting means having a gap therein through which the unattached portions of the elastic ribbon move away from the web along a second path, said first path along the supporting means being longer than the second path whereby the unattached portions of the elastic ribbon are separated from the web.

4. The combination according to claim 3 wherein the elastic ribbon is in a stretched condition as it moves through said apparatus whereby the unattached portions of the ribbon will readily move through said gap to thereby attain a relatively relaxed condition.

5. The combination according to claim 3 wherein the support means comprises an arcuate surface and the gap comprises a gap through the arcuate surface.

6. The combination according to claim 3 wherein the support means comprises a plurality of rollers and the gap comprises a space between facing ends of the rollers.

7. The combination according to claims 1, 3 or 4 wherein said removing means includes means for holding the unattached portions of the moving elastic ribbon part from the web and means for cutting both ends of the unattached ribbon portions.

8. The combination according to claim 7 wherein said holding means comprises vacuum means.

9. The combination according to claim 8 wherein the vacuum means comprises a vacuum drum including a rotating cylindrical drum wall and a vacuumized stationary compartment within said drum having an opening facing the interior said of said drum wall, said opening having a length equal to the linear length of travel of the drum wall along which it is desired to hold the elastic ribbon, said drum wall having at least one opening rotating with the drum wall opposite the vacuumized compartment opening and in close proximity to the unattached portion of the elastic ribbon whereby said unattached ribbon portion is exposed to the vacuum and held against the drum wall by the vacuum to thereby tension the unattached ribbon portion during cutting and carry the cut unattached ribbon piece away after cutting as the drum wall rotates.

10. In a method for manufacturing elastic leg disposable diapers including continuously moving a web of material and a ribbon of elastic material into engagement with each other and attaching portions of the elastic ribbon to the web along spaced apart locations on the length of the web corresponding to the leg areas of the finished diapers, the steps comprising:
   during the travel of the web and elastic ribbon together, supporting the web along a path of movement that is longer than the path of movement of the portion of the elastic ribbon between the attached spaced apart locations whereby said portion of the elastic ribbon is separated from the web along the longer path of movement of the web; and
   removing at least a part of the separated portion of the elastic ribbon whereby the ribbon will have an elasticization affect only along the attached locations corresponding to the leg areas of the finished diapers.

11. The method according to claim 10 wherein, during the supporting of the web, the portion of the elastic ribbon between the attached spaced apart locations is drawn along a path of movement that is shorter than said path of movement of the web.

12. The method according to claim 10 wherein elongating tension is applied to the elastic ribbon such that the portion of the elastic ribbon between the spaced apart locations readily contracts to a separated shorter path of movement than that of the web during supporting of the web along its relatively longer path of movement.

13. The method according to claim 12 wherein the step of removing the separated portion of the elastic ribbon includes cutting the separated portion of the elastic ribbon subsequent to applying the elongating tension to the separated portion of the elastic ribbon to thereby increase the speed of cutting of the ribbon.

14. The method according to claim 10 or 13 wherein said removing step includes cutting both ends of the separated portion of the elastic ribbon.

15. The method according to claim 14 where said removing step includes applying a vacuum to the separated portion of the elastic ribbon to carry it away subsequent to said cutting.

16. The method according to claim 14 wherein said removing step includes increasing the tension on the separated portion of the elastic ribbon by holding the ribbon with a vacuum and moving the area of application of the vacuum and thereby the separated portion of the ribbon in a direction away from the point of attachment of the separated portion of the ribbon with the portion of the ribbon attached to the web.

* * * * *